United States Patent [19]

Hansen

[11] Patent Number: 5,260,298
[45] Date of Patent: Nov. 9, 1993

[54] IMIDAZATRIAZOLOQUINAZOLINE COMPOUNDS AND THEIR USE

[75] Inventor: Holger C. Hansen, Vaerlose, Denmark

[73] Assignee: Novo Nordisk A/S, Bagsvaerd, Denmark

[21] Appl. No.: 839,981

[22] Filed: Feb. 20, 1992

[30] Foreign Application Priority Data

Mar. 7, 1991 [DK] Denmark ............... DK0411/91

[51] Int. Cl.⁵ ............... A61K 31/505; C07D 487/14
[52] U.S. Cl. ............... 514/257; 544/247; 544/250
[58] Field of Search ............... 544/247; 514/257

[56] References Cited

U.S. PATENT DOCUMENTS

| | | | |
|---|---|---|---|
| 4,774,245 | 9/1988 | Wätjen et al. | 514/250 |
| 5,100,895 | 3/1992 | Hansen et al. | 544/247 |

FOREIGN PATENT DOCUMENTS 417027  3/1991  European Pat. Off. ........... 544/247

*Primary Examiner*—Emily Bernhardt
*Attorney, Agent, or Firm*—Steve T. Zelson; Karen A. Lowney

[57] ABSTRACT

Imidazotriazoloquinazoline compounds having the general formula

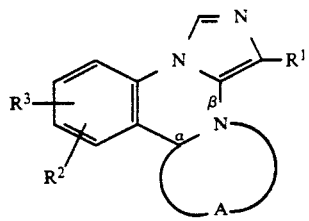

wherein A together with the α-marked carbon atom and the β-marked nitrogen atom is one of the groups

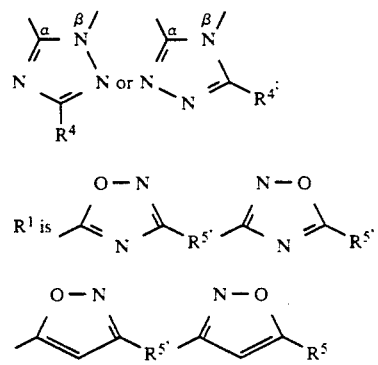

cyano or $CO_2R^5$, wherein $R^5$ is H, alkyl, cycloalkyl, trifluoromethyl or alkoxymethyl; and $R^2$, $R^3$ and $R^4$ independently are H, hydroxy, halogen, CN, alkyl, alkenyl, alkynyl, trifluoromethyl, alkoxy, dialkylaminoalkoxy, aralkoxy, aryloxy which may be substituted, acyclic amino group, or $NR^6R^7$, wherein $R^6$ and $R^7$ independently are H or alkyl.

The compounds are useful in psychopharmaceutical preparations as anticonvulsants, anxiolytics, hypnotics, antipsychotics, antiemetics, or in improving the cognitive function of the brain of mammals, or as benzodiazepine antagonsists.

11 Claims, No Drawings

IMIDAZATRIAZOLOQUINAZOLINE COMPOUNDS AND THEIR USE

The present invention relates to therapeutically active tetracyclic imidazotriazoloquinazoline compounds, a method of preparing the same, pharmaceutical compositions comprising the compounds, and to methods of treating therewith. The novel compounds are useful in psychopharmaceutical applications, e.g., in the treatment of central nervous system ailments, for example, as anti-convulsants, anxiolytics, hypnotics, antipsychotics, antiemetics, in improving the cognitive function of the brain of mammals, or as benzodiazepine antagonists.

It is well known (Squires, R. F. and Braestrup, C. in Nature (London) 266 (1977) 732-734) that specific sites in the central nervous systems of vertebrates exhibit a high specific affinity for binding 1,4- and 1,5-benzodiazepines. These sites are called benzodiazepine receptors.

It has now been found that members of a novel group of tetracyclic imidazotriazoloquinazoline compounds have strong affinity for the benzodiazepine receptors which make them useful in psychopharmaceutical preparations.

Accordingly, it is an object of the invention to provide such novel tetracyclic imidazotriazoloquinazoline compounds.

The compounds of the invention have the general formula I

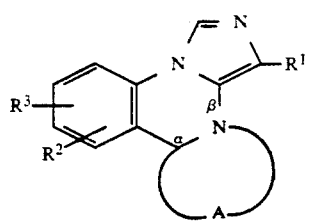
(I)

and pharmaceutically acceptable acid addition salts thereof, wherein A together with the α-marked carbon atom and the β-marked nitrogen atom is one of the groups

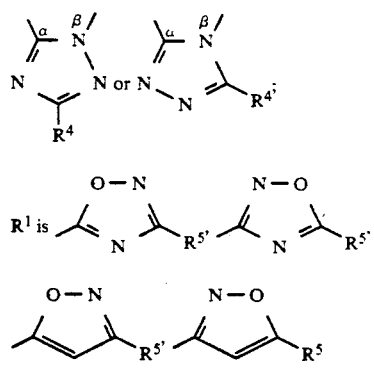

cyano or $CO_2R^5$, wherein $R^5$ is hydrogen, $C_{1-6}$-alkyl, $C_{3-7}$-cycloalkyl, trifluoromethyl or $C_{1-6}$-alkoxymethyl; and $R^2$, $R^3$ and $R^4$ independently are hydrogen, hydroxy, halogen, CN, $C_{1-6}$-alkyl, $C_{2-6}$-alkenyl, $C_{2-6}$-alkynyl, trifluoromethyl, $C_{1-6}$-alkoxy, dialkylaminoalkoxy, aralkoxy, aryloxy which may be substituted with halogen or alkoxy, a cyclic amino group, or $NR^6R^7$, wherein $R^6$ and $R^7$ independently are hydrogen or $C_{1-6}$-alkyl.

The invention also relates to methods of preparing the above mentioned compounds. These methods comprise:

a) reacting a compound of formula II

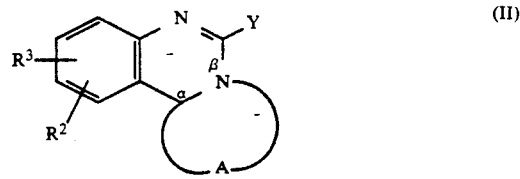
(II)

wherein A, $R^2$ and $R^3$ are as defined above and wherein Y is a leaving group, with a compound having the formula III $$CN-CH_2-R^1 \quad \text{(III)}$$

wherein $R^1$ is as defined above, to form a compound of the invention, or b) reacting a reactive derivative of a compound having the general formula IV

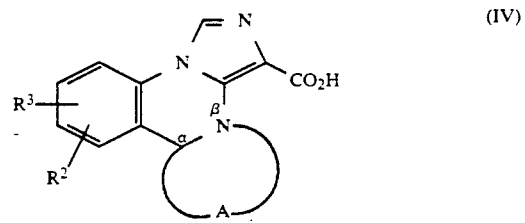
(IV)

wherein A, $R^2$ and $R^3$ are as defined above with a compound having the general formula V $$R^5-C(=NOH)NH_2 \quad \text{(V)}$$

wherein $R^5$ is as defined above to form a compound of the general formula I wherein $R^1$ is

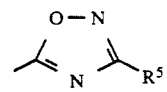

wherein $R^5$ is as defined above, or c) reacting a compound of the general formula VI

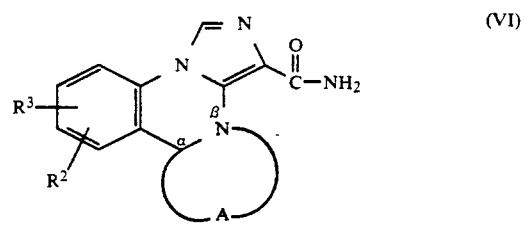
(VI)

wherein —A—, $R^2$ and $R^3$ have the meanings set forth above, with a dehydrating agent to form a compound of formula I, wherein —A—, $R^2$ and $R^3$ have the meanings set forth above and wherein $R^1$ is cyano, or d) reacting a compound of formula VII

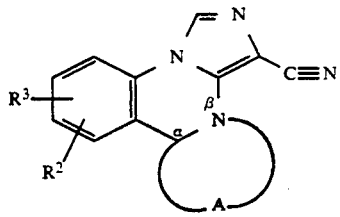

wherein —A—, $R^2$ and $R^3$ have the meaning set forth above, with $NH_2OH$ to form a compound of formula VIII

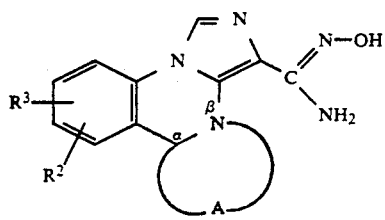

wherein —A—, $R^2$, and $R^3$ have the meanings set forth above, and reacting the compound of formula VIII with $R^5$—COCl or with $(R^5CO)_2O$, wherein $R^5$ is as defined above to form a compound of the general formula I wherein $R^1$ is

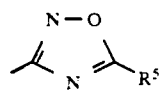

where $R^5$ is as defined above.

The leaving group, Y, may be any suitable leaving group and, for example, those disclosed in U.S. Pat. Nos. 4,031,079 or 4,359,420, for example, halogen, alkylthio, e.g., methylthio, aralkylthio, N-nitrosoalkylamino, alkoxy mercapto, —OP(O)(OR)$_2$ wherein R is lower-alkyl or —OP(O)(NR'R")$_2$ wherein R' and R" each represents lower-alkyl or phenyl, or together with the nitrogen atom to which they are attached represent a heterocyclic radical such as morpholino, pyrrolidino, piperidino, or methylpiperazino. The reaction is preferably carried out under alkaline conditions, i.e., in the presence of a base, and among bases alkali metal (e.g., potassium or sodium) alkoxides or hydrides are preferred. The reaction is preferably conducted in the presence of an organic solvent which is nonreactive with the reactants and products of reaction under the conditions of reaction, especially an anhydrous solvent and preferably an anhydrous aprotic solvent such as dimethylformamide (DMF), tetrahydrofuran (THF), or the like. The temperature range employed may be any range suitable for the reaction to proceed at a reasonable rate and without undue delay or decomposition and a range from about minus forty (—40) degrees Celsius to about room temperature is accordingly usually particularly suitable.

The starting materials employed in the syntheses of the compounds of formula I are either known or may be prepared in conventional manner from commercially available materials, see e.g. J. E. Francis et al., J. Med. Chem. 34, 281 (1991) and references cited therein.

The isocyanomethyloxadiazoles of formula III may be prepared as described in the prior art, e.g. U.S. Pat. No. 4,774,245. 3(5)-Alkyl-5(3)-halomethylisoxazoles, either known or prepared from appropriate starting materials according to known procedures (e.g. U.S. Pat. No. 3,290,301 and Ger. Offen. DE 25 49 962), may by conventional techniques be converted to 3(5)-alkyl-5(3)-aminomethylisoxazoles which in turn may be N-formylated and subsequently dehydrated to give isocyanomethylisoxazoles.

The pharmaceutical properties of the compounds of the invention can be illustrated by determining their capability for displacing radioactive labelled flunitrazepam from benzodiazepine receptors.

The displacement activity of the compounds of the invention may be found by determining the $ED_{50}$ value. The $ED_{50}$ value represents the dose (mg/kg) of a test substance which causes the specific binding of $^3$H-flunitrazepam to benzodiazepine receptors in a living brain to be reduced to 50% of the control value.

Such an in vivo test is carried out as described in U.S. Pat. No. 4,774,245.

Test results obtained by testing some compounds of the invention will appear from the following table I.

TABLE I

| Compound | $ED_{50}$ (mg/kg) |
|---|---|
| 3 | 0.16 |
| 5 | 0.30 |

The compound of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one tenth (0.1) milligram of active ingredient or, more broadly, one tenth (0.1) to hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyathoxylated castor oil, gelatin, lactose, amylose, magnesium stearate, talc, silicic acid, fatty acid monoglycerides and diglycerides, pentaerythritol fatty acid esters, hyroxymethylcellulose and polyvinylpyrrolidone.

The pharmaceutical preparations can be sterilized and mixed, if desired, with auxilliary agents, such as lubricants, preservatives, stabilizers, wetting agents, emulsifiers, salt for influencing osmotic pressure, buffers and/or coloring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05–100 mg in a pharmaceutically-acceptable carrier per unit dosage. A typical tablet which may be prepared by conventional tabletting techniques contains:

| Active compound | 1.0 mg |
| --- | --- |
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

Due to their high degree of affinity for the benzodiazepin receptors, receptors, the compounds of the invention are extremely useful in the treatment of central nervous system ailments or disorders, when administered in an amount effective for the alleviation, amelioration, or elimination thereof. The important CNS activity of the compounds of the invention includes both anticonvulsant, hypnotic, nootropic and anxiolytic activities along with a low toxicity, together presenting a most favorable therapeutic index. The compounds of the invention may accordingly be administered to a subject, e.g., a living mammal body, including a human, in need of the same for the treatment, alleviation, amelioration, or elimination of an indication, associated with the central nervous system and the socalled benzodiazepine receptors, which requires such psychopharmaceutical treatment, e.g., especially convulsion, insomnia, anxiety and/or dementia states, if desired in the form of a pharmaceutically acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g., an anticonvulsant and/or anxiolytic amount, and in any event an amount which is effective for the alleviation of such a central nervous system ailment due to their benzodiazepine receptor affinity. Suitable dosage ranges are 1-200 milligrams daily, 1-100 milligrams daily, and especially 1-30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples, which may not be construed as limiting:

EXAMPLE 1

5-(5-cyclopropyl-1,2,4-oxadiazol-3-yl)-imidazo[1,5-a]-1,2,4-triazolo[4,3-c]quinazoline (compound 1)

To a stirred slurry of 5-chloro-1,2,4-triazolo[4,3-c]quinazoline (3.5 g, 17 mmol) in 40 ml of dry DMF at 10° C. was first added 5-cyclopropyl-3-isocyanomethyl-1,2,4-oxadiazole (purity 80%, 3.4 g, 18 mmol) and then a solution of potassium tert-butoxide (2.55 g, 23 mmol) in 40 ml of DMF, allowing the temperature to rise to room temperature. After ½ h the mixture was filtered and the filter cake washed with water and finally with ether and dried, giving the title compound as colorless crystals, m.p. 308°–314° C.

$^1$H-NMR (CDCl$_3$) δ: 10.50 (s, 1H, triazolo-) 8.52 (s, 1H, imidazo), 8.7–7.64 (m, 4H, benzo-), 2.45–2.34 (m, 1H, CH), 1.48–1.32 (m, 4H, CH$_2$). MS: m/e 317 (M$^+$), 250, 166, 129, 102, 69.

EXAMPLE 2

5-cyclopropyl-1,2,4-oxadiazol-3-yl)-imidazo[1,5-a]-[1,2,4]triazolo[1,5-c]quinazoline (compound 2)

A stirred mixture of crude 5-chloro-[1,2,4]triazolo[1,5-c]quinazoline (1.0 g, 4.9 mmol) and 5-cyclopropyl-3-isocyanomethyl-1,2,4-oxadiazole (purity 80%, 1.16 g, 6.2 mmol) in 20 ml of dry dimethylformamide (DMF) was cooled to 0° C. Solid potassium tert-butoxide (1.15 g, 10 mmol) was added gradually, keeping the temperature below 5° C., whereafter the mixture was stirred at room temperature for 45 minutes. Then the mixture was stirred at 0° C. for ½ h and the precipitated product was collected by filtration, rinsed on the filter with water and dried. Yield 0.64 g. An additional amount of product, 0.5 g, precipitated from the mother liqueour by addition of water. The combined crops of crystals was stirred with isopropyl alcohol at 60° C., cooled to room temperature and filtered. The filter cake was dried to give 0.73 g of the title compound m.p. 230°–233° C.

$^1$H-NMR (CDCl$_3$)δ: 8.57 (s, 1H, imidazo-), 8.40 (s, 1H, triazolo-), 8.52–7.55 (m, 4H, benzo-), 2.46–2.26 (m, 1H, CH), 1.5–1.2 (m, 4H, CH$_2$); MS: m/e 317 (M$^+$), 250, 195, 166, 129, 102, 69.

In the same way the following compounds were prepared:

5-(3-cyclopropyl-1,2,4-oxadiazol-5-yl)-imidazo[1,5-a]-[1,2,4]triazolo[1,5-c]quinazoline, m.p. 267°–269°C., $^1$H-NMR (CF$_3$COOD)δ: 9.68 (s, 1H), 9.09 (s, 1H), 8.88– 8.02 (m, 4H), 2.50–2.28 (m, 1H , 163–1.2 (m, 4H); prepared from 5-chloro-[1,2,4]triazolo[1,5-c]quinazoline and 3-cyclopropyl-5-isocyanomethyl-1,2,4-oxadiazole. (compound 3)

5-(5-cyclopropyl-1,2,4-oxadiazol-3-yl)-2-methyl-imidazo[1,5-a][1,2,4]triazolo[1,5-c]quinazoline, m.p. 280°–283° C., MS: m/e 332 (M+1), 331, 264, 129, 102, 69; prepared from 5-chloro-2-methyl-[1,2,4]triazolo[1,5-c]quinazoline and 5-cyclopropyl-3-isocyanomethyl-1,2,4-oxadiazole. (compound 4)

12-chloro-5-(3-cyclopropyl-1,2,4-oxadiazol-5-yl)-imidazo[1,5-a][1,2,4]triazolo[1,5-c]quinazoline, m.p. 278°–284° C., MS: m/e 351/353 (M$^+$/M$^+$+2), 270/272, 268, 163; prepared from 5,10-dichloro-[1,2,4]triazolo[1,5-c]quinazoline and 3-cyclopropyl-5-isocyanomethyl-1,2,4-oxadiazole. (compound 5)

12-chloro-5-(5-cyclopropyl-1,2,4-oxadiazol-3-yl)imidazo[1,5-a][1,2,4]triazolo[1,5-c]quinazoline, m.p. 262°-263° C., MS: m/e 351/353 (M+/M++2), 268, 229, 200, 163, 136, 100, 69; prepared from 5,10-dichloro-[1,2,4]triazolo[1,5-c]quinazoline and 5-cyclopropyl-3-isocyanomethyl-1,2,4-oxadiazole. (compound 6)

5-(3-cyclopropyl-1,2,4-oxadiazol-5-yl)-11-methylimidazo[1,5-a][1,2,4]triazolo[1,5-c]quinazoline, m.p. 271°-273° C., MS: m/e 331 (M+), 250, 248, 222, 209, 143, 116, 89, 53; prepared from 5-chloro-9-methyl-[1,2,4]triazolo[1,5-c]quinazoline and 3-cyclopropyl-5-isocyanomethyl-1,2,4-oxadiazole. (compound 7)

5-(5-cyclopropyl-1,2,4-oxadiazol-3-yl)-11-methylimidazo[1,5-a][1,2,4]triazolo[1,5-c]quinazoline, m.p. 280°-282° C., MS: m/e 331 (M+), 264, 248, 209, 181, 143, 116, 89, 69; prepared from 5-chloro-9-methyl-[1,2,4]triazolo[1,5-c]quinazoline and 5-cyclopropyl-3-isocyanomethyl-1,2,4-oxadiazole. (compound 8)

5-(5-methyl-1,2,4-oxadiazol-3-yl)-12-methylimidazo[1,5-a][1,2,4]triazolo[1,5-c]quinazoline, m.p. 265°-269° C., MS: m/e 305 (m+), 263, 210, 184, 181, 157, 89, 43; prepared from 5-chloro-10-methyl-[1,2,4]triazolo[1,5-a]quinazoline and 3-isocyanomethyl-5-methyl-1,2,4-oxadiazole. (Compound 9)

5-(5-cyclopropyl-1,2,4-oxadiazol-3-yl)-12-methyl-imidazo[1,5-a][1,2,4]triazolo[1,5-c]quinazoline, m.p. 254°-256° C., MS: m/e 331 (M+), 263, 69; prepared from 5-chloro-10-methyl-[1,2,4]triazolo[1,5-a]quinazoline and 5-cyclopropyl-3-isocyanomethyl-1,2,4-oxadiazole. (compound 10)

12-chloro-5-(5-cyclopropyl-1,2,4-oxadiazol-3-yl)-2-methyl-imidazo[1,5-a][1,2,4]triazolo[1,5-c]quinazoline, m.p. 210-213, MS: m/e 365, 298, 69; prepared from 5,10-dichloro-2-methyl-[1,2,4]triazolo[1,5-c]quinazoline and 5-cyclopropyl-3-isocyanomethyl-1,2,4-oxadiazole. (Compound 11)

I claim:

1. A tetracyclic imidazotriazoloquinazoline compound having the formula I:

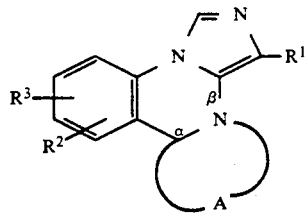

wherein A together with the α-marked carbon atom and the β-marked nitrogen atom is one of the groups

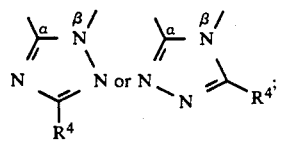

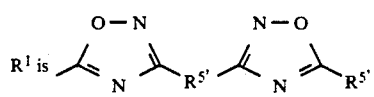

cyano or $CO_2R^5$, wherein $R^5$ is hydrogen, $C_{1-6}$-alkyl, $C_{3-7}$-cycloalkyl, trifluoromethyl, or $C_{1-6}$-alkoxymethyl; and $R^2$, $R^3$ and $R^4$ independently are hydrogen, hydroxy, halogen, CN, $C_{1-6}$-alkyl, $C_{2-6}$-alkenyl, $C_{2-6}$-alkynyl, trifluoromethyl, $C_{1-6}$-alkoxy, dialkylaminoalkoxy, aralkoxy, aryloxy which may be substituted with halogen or alkoxy, or $NR^6R^7$, wherein $R^6$ and $R^7$ independently are hydrogen or $C_{1-6}$alkyl, or a pharmaceutically acceptable acid addition salt thereof.

2. The compound of claim 1 in which $R^2$, $R^3$ or $R^4$ are independently hydrogen, halogen or $C_{1-6}$alkyl.

3. A compound which is 5-(5-cyclopropyl-1,2,4-oxadiazol-3-yl)-imidazol[1,5-a][1,2,4]triazolo[1,5-c]quinazoline.

4. A compound which is 5-(3-cyclopropyl-1,2,4-oxadiazol-5-yl)-imidazo[1,5-a][1,2,4triazolo[1,5-c]quinazoline.

5. A compound which is 12-chloro-5-(3-cyclopropyl-1,2,4-oxadiazol-5-yl)-imidazo[1,5-a][1,2,4triazolo-[1,5-c]quinazoline.

6. A compound which is 12-chloro-5-(5-cyclopropyl-1,2,4-oxadiazol-3-yl)-imidazol[1,5-a][1,2,4]triazolo-[1,5-c]quinazoline.

7. A tetracyclic imidazotriazoloquinazoline compound having the formula I:

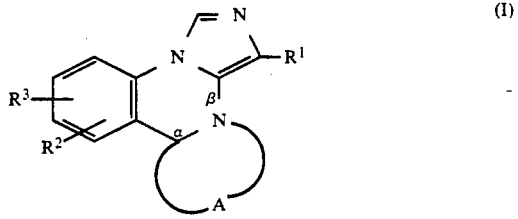

wherein A together with the α-marked carbon atom and the β-marked nitrogen atom is one of the groups

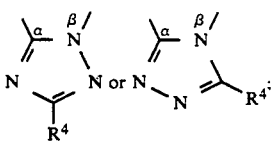

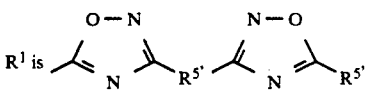

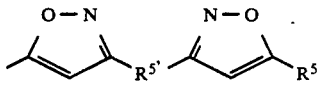

cyano or $CO_2R^5$, wherein $R^5$ is hydrogen, methyl, cyclopropyl, trifluoromethyl or $C_{1-6}$-alkoxymethyl; and $R^2$, $R^3$ and $R^4$ independently are hydrogen, hydroxy, halogen, CN, methyl, trifluoromethyl, $C_{1-6}$-alkoxy, dialkylaminoalkoxy, or a pharmaceutically acceptable acid addition salt thereof.

8. A pharmaceutical composition comprising (a) as active component tetracyclic imidazotriazoloquinazoline compound having the formula I:

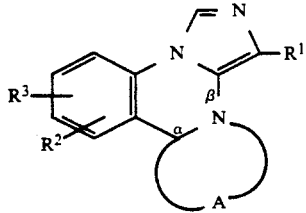
(I)

wherein A together with the α-marked carbon atom and the β-marked nitrogen atom is one of the groups

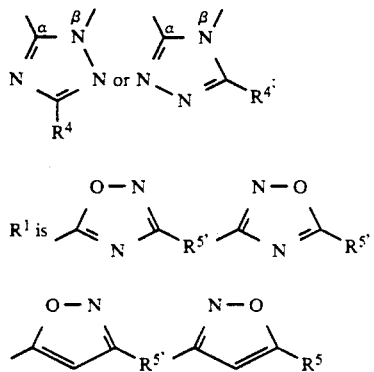

cyano or $CO_2R^5$, wherein $R^5$ is hydrogen, $C_{1-6}$-alkyl, $C_{3-7}$-cycloalkyl, trifluoromethyl, or $C_{1-6}$-alkoxymethyl; and $R^2$, $R^3$ and $R^4$ independently are hydrogen, hydroxy, halogen, CN, $C_{1-6}$-alkyl, $C_{2-6}$-alkenyl, $C_{2-6}$-alkynyl, trifluoromethyl, $C_{1-6}$-alkoxy, dialkylaminoalkoxy, aralkoxy, aryloxy which may be substituted with halogen or alkoxy, or $NR^6R^7$, wherein $R^6$ and $R^7$ independently are hydrogen or $C_{1-6}$-alkyl, or a pharmaceutically acceptable acid addition salt thereof and (b) a pharmaceutically acceptable carrier or diluent.

9. The pharmaceutical composition according to claim 8 wherein it is in the form of an oral dosage unit containing 0.1-100 mg of the active compound.

10. A method of treating a central nervous system ailment associated with benzodiazepine receptors in a subject in need of such treatment comprising the step of administering to said subject an amount of a tetracyclic imidazotriazoloquinazoline compound effective for the alleviation of such ailment having the formula I:

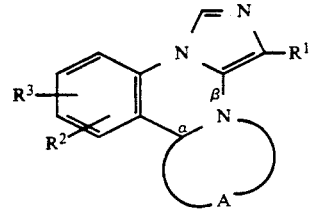
(I)

wherein A together with the α-marked carbon atom and the β-marked nitrogen atom is one of the groups

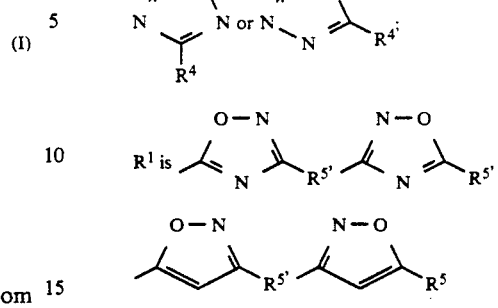

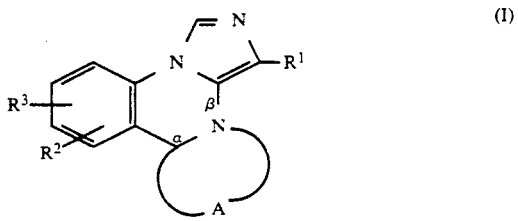

cyano or $CO_2R^5$, wherein $R^5$ is hydrogen, $C_{1-6}$-alkyl, $C_{3-7}$-cycloalkyl, trifluoromethyl, or $C_{1-6}$-alkoxymethyl; and $R^2$, $R^3$ and $R^4$ independently are hydrogen, hydroxy, halogen, CN, $C_{1-6}$-alkyl, $C_{2-6}$-alkenyl, $C_{2-6}$-alkynyl, trifluoromethyl, $C_{1-6}$-alkoxy, dialkylaminoalkoxy, aralkoxy, aryloxy which maybe substituted with halogen or alkoxy, or $NR^6R^7$-wherein $R^6$ and $R^7$ independently are hydrogen or $C_{1-6}$alkyl, or a pharmaceutically acceptable acid addition salt thereof.

11. A method of treating a central nervous system ailment associated with benzodiazepine receptors in a subject is need of such treatment comprising the step of administering to said subject an amount of a composition effective for the alleviation of such ailment, said composition comprising (a) a tetracyclic imidazotriazoloquinazoline having the formula I:

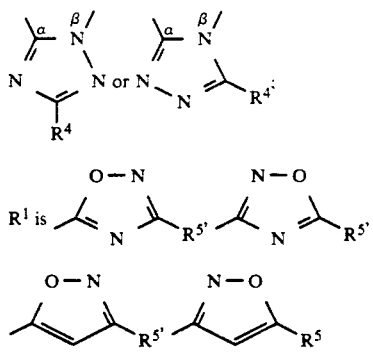
(I)

wherein A together with the α-marked carbon atom and the βmarked nitrogen atom is one of the groups

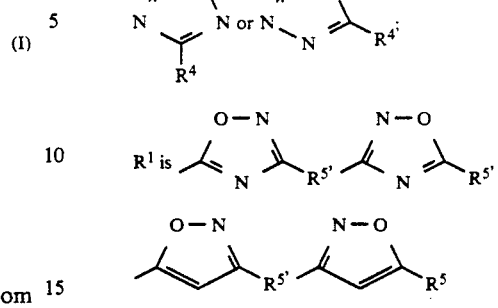

cyano or $CO_2R^5$, wherein $R^5$ is hydrogen, $C_{1-6}$-alkyl, $C_{1-7}$-cycloalkyl, trifluoromethyl, or $C_{1-6}$-alkoxymethyl; and $R^2$, $R^3$ and $R^4$ independently are hydrogen, hydroxy, halogen, CN, $C_{1-6}$-alkyl, $C_{2-6}$-alkenyl, $C_{2-6}$-alkynyl, trifluoromethyl, $C_{1-6}$-alkoxy, dialkylaminoalkoxy, aralkoxy, aryloxy which may be substituted with halogen or alkoxy, or $N^6R^7$-wherein $R^6$ and $R^7$ independently are hydrogen or $C_{1-6}$alkyl, or a pharmaceutically acceptable acid addition salt thereof. and (b) a pharmaceutically acceptable carrier or diluent.

* * * * *